(12) United States Patent
Seghers et al.

(10) Patent No.: US 7,210,334 B2
(45) Date of Patent: May 1, 2007

(54) DEVICE FOR DETERMINING THE FINENESS OF MINERAL FIBERS

(75) Inventors: Alex Seghers, Fitz James (FR); Gilles Boyer, Lesperon (FR)

(73) Assignee: Saint-Gobain Isover, Courbevoie (FR)

(*) Notice: Subject to any disclaimer, the term of this patent is extended or adjusted under 35 U.S.C. 154(b) by 51 days.

(21) Appl. No.: 10/510,705

(22) PCT Filed: May 7, 2003

(86) PCT No.: PCT/FR03/01419

§ 371 (c)(1),
(2), (4) Date: May 9, 2005

(87) PCT Pub. No.: WO03/098209

PCT Pub. Date: Nov. 27, 2003

(65) Prior Publication Data

US 2005/0235736 A1    Oct. 27, 2005

(30) Foreign Application Priority Data

May 22, 2002 (FR) .................................. 02 06252

(51) Int. Cl.
*G01N 15/08* (2006.01)
(52) U.S. Cl. ........................................................ 73/38
(58) Field of Classification Search ..................... 73/38
See application file for complete search history.

(56) References Cited

U.S. PATENT DOCUMENTS

| | | | |
|---|---|---|---|
| 2,919,573 A * | 1/1960 | Berkley et al. ................. 73/38 |
| 3,039,293 A * | 6/1962 | Reddick et al. ................. 73/38 |
| 3,116,629 A * | 1/1964 | Neil ............................... 73/38 |
| 4,311,037 A * | 1/1982 | Gotchel et al. ................. 73/38 |
| 4,396,943 A   | 8/1983 | Lord et al. |
| 4,440,021 A   | 4/1984 | Abouchar et al. |
| 4,649,738 A * | 3/1987 | Waldie et al. .................. 73/38 |
| 4,891,967 A * | 1/1990 | Vogt ............................... 73/38 |
| 5,359,880 A   | 11/1994 | Elam et al. |
| 5,544,520 A * | 8/1996 | Graf et al. ....................... 73/38 |
| 5,576,480 A * | 11/1996 | Hopkins et al. ................ 73/38 |
| 5,892,142 A * | 4/1999 | Ghorashi et al. ............... 73/38 |
| 6,543,275 B2 * | 4/2003 | Wu et al. ........................ 73/38 |
| 2004/0187560 A1 * | 9/2004 | Cholet ............................. 73/38 |

FOREIGN PATENT DOCUMENTS

| | | |
|---|---|---|
| EP | 0 373 058 | 6/1990 |
| JP | 59170745 A * | 9/1984 |

* cited by examiner

*Primary Examiner*—Hezron Williams
*Assistant Examiner*—John Fitzgerald
(74) *Attorney, Agent, or Firm*—Oblon, Spivak, McClelland, Maier & Neustadt, P.C.

(57) ABSTRACT

An apparatus for determining the fineness index of mineral fibers, designed to deliver the micronaire value of fibers. The apparatus includes a device for measuring the fineness index provided with at least a first orifice connected to a measurement cell configured to hold a specimen of a plurality of fiber and provided with a second orifice connected to a device for measuring a differential pressure, on either side of the specimen. The device measuring the differential pressure is configured to be connected to a device for producing a fluid flow. The device for measuring the fineness index also includes at least one flowmeter for measuring the volume flow rate of the fluid passing through the cell.

16 Claims, 2 Drawing Sheets

DEVICE FOR DETERMINING THE FINENESS OF MINERAL FIBERS

CROSS-REFERENCE TO RELATED APPLICATIONS

Figure 1:
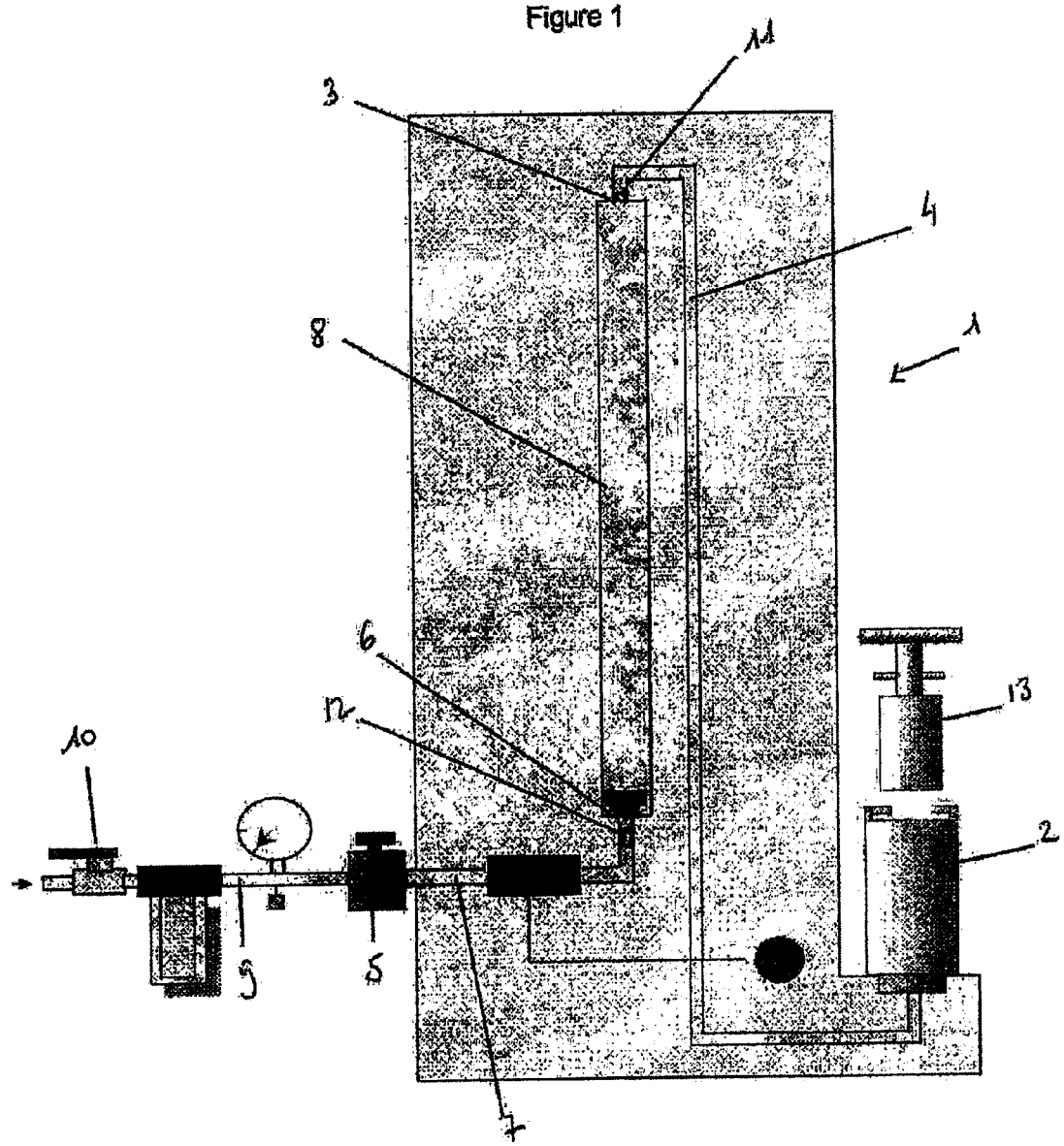

The present application is the U.S. counterpart of WO 03/098209 and in turn claims priority of French Application No. 02/06252 filed on May 22, 2002, the entire contents of each of which are hereby incorporated herein by reference.

The present invention relates to an apparatus for determining the fineness of mineral fibres, these fibres being intended especially for the industrial manufacture of glass wool to be used, for example, in making up thermal and/or acoustic insulation products. It also relates to a method of measuring the fineness of mineral fibres and to the application of this apparatus to the measurement of the fineness of hyperfine fibres.

More precisely the aim is to allow the value of their "micronaire" (F) to be determined.

It is known in this technical field to measure the "micronaire" in order to characterize the fineness index, this index, accounting for the specific surface area, being determined by measuring the aerodynamic pressure drop when a given quantity of fibres, containing no binder, is subjected to a given pressure of a gas, generally air or nitrogen.

This measurement is commonplace in natural fibre (especially cotton fibre) production units and is standardized according to the DIN 53941, ASTM 1994, D 4604-86, D 4605-86 or EN 29053 standards and it uses an apparatus called a "micronaire apparatus" as described for example in EP 0 373 058.

In addition, it should be noted that the mass of the specimen is generally of the order of 10 g and may, according to the recommendations most commonly employed, be up to 50 g when the fibres are cotton fibres.

On the basis of these teachings, a micronaire apparatus has been developed, and is widely used, which gives, using a device for measuring the fineness index of mineral fibres, which is graduated in "micronaire" values, reliable measurements for mean fibre diameters of between about 3 and 9 µm and within this mean diameter range. This mean diameter is calculated from the histogram measured in a microscope (×1000) on 200 fibres.

Manufacturers, in their constant search to improve the overall heat exchange coefficient and/or to reduce the density of products for the same thermal capacity, are increasingly having to produce fibres (called hyperfine fibres in the rest of the text) whose mean diameter is constantly being reduced and tends to lie in the range from 2 to 3 µm, or even much lower.

However, in these hyperfine fibre manufacturing ranges, the "micronaire" measurement described above is not possible.

However, such manufacture of hyperfine fibres needs to have a measurement instrument for monitoring, practically in real time, the manufacturing process so as to be able to rapidly intervene in the process should there be a malfunction.

For the sake of rationalization, the assumption adopted was to retain the principle of the conventional micronaire apparatus, this apparatus having proven its effectiveness in the case of mineral fibres whose diameter is greater than 3 µm and whose advantages are appreciated by professionals in the technical field in question (easy implementation, great simplicity, reliability, speed of implementation, economics, etc).

Based on this observation and knowing the inability of this micronaire apparatus to deliver measurements for hyperfine fibres, the aim of the present invention is to provide a micronaire apparatus designed to deliver micronaire values for hyperfine fibres, the mean diameter of which is less than 3 µm.

An apparatus is known for determining the fineness index of fibres which is designed to deliver the micronaire value of mineral fibres whose mean diameter is substantially greater than 3 µm, comprising a device for measuring the fineness index, the said device for measuring the fineness index being provided, on the one hand, with at least a first orifice connected to a measurement cell designed to hold a specimen consisting of a plurality of fibres and, on the other hand, with a second orifice connected to a device for measuring a differential pressure, on either side of the said specimen, the said device for measuring the differential pressure being intended to be connected to a device for producing a fluid flow.

For this purpose, according to the invention, an apparatus for determining the fineness index of the kind in question is characterized in that the device for measuring the fineness index includes at least one flowmeter for measuring the volume flow rate of the gas passing through the said cell.

By virtue of these arrangements, a micronaire value for hyperfine fibres is rapidly obtained using a conventional apparatus for determining the fineness index without having to modify its calibration and its operating conditions (quantity of fibres introduced into the cell, value of the differential pressure, etc).

In preferred embodiments of the invention, one or both of the following provisions may furthermore be optionally adopted:
 the volume flowmeter consists of a volume flowmeter graduated in l/min;
 one of the orifices includes a calibrated member.

According to another aspect of the invention, this also relates to a method of measuring the fineness of fibres using an apparatus for determining the fineness of mineral fibres as indicated above, characterized in that:
the measurement cell is filled with a specimen of fibres, the specimen mass being determined in such a way that the specimen occupies the entire volume of the said measurement cell so that there is no preferential flow of gas within the specimen;
the value of the differential pressure between the upstream end and the downstream end of the specimen is adjusted after the said cell has been closed using a lid;
the said measurement apparatus is connected to a device for producing a flow of fluid; and
the measurement is taken using the volume flowmeter.

In preferred ways of implementing the invention, one or both of the following provisions may optionally furthermore be adopted:
 the entire volume of the measurement cell is filled with a specimen of fibres, the mass of which is equal to at least 5 g, preferably between 5 and 10 g, and even more preferably equal to 5 g;
 a differential pressure, the value of which is approximately 254 mmHg, is applied.

According to yet another aspect of the invention, this also relates to the application of the measurement apparatus described above to the measurement of the fineness index for hyperfine insulation fibres (mean diameter less than 3 µm), especially glass wool, particularly those obtained by an internal centrifuging process.

Other features and advantages of the invention will become apparent in the course of the following description of one of its embodiments, given by way of non-limiting example and with regard to the appended drawings.

Figure 2:
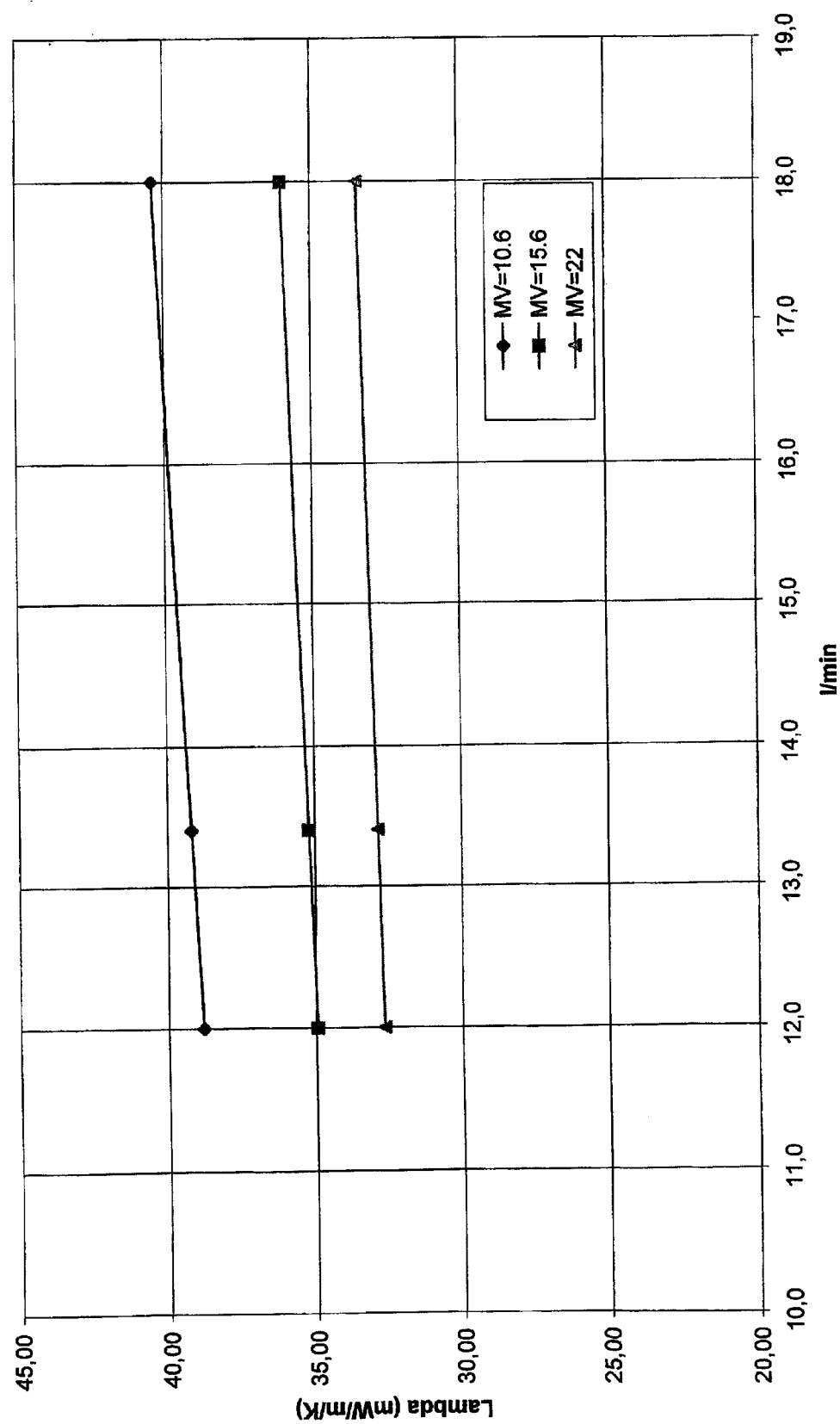

In the drawings:

FIG. 1 is a schematic view of a "micronaire" apparatus according to the invention; and FIG. 2 gives the value of the thermal conductivity coefficient for various fibre densities as a function of the micronaire value expressed in l/min.

In the various figures, the same references denote identical or similar elements.

FIG. 1 shows a micronaire apparatus according to the invention. This apparatus 1 includes a measurement cell 2, which is preferably cylindrical. This cell 2 is designed to hold a specimen of fibres, for which it is desired to measure their fineness.

This apparatus also includes a device 8 for measuring the fineness index.

This device 8 for measuring the fineness index has at least a first orifice 3 connected via a first pipe 4 to the measurement cell 2 designed to hold the specimen formed by a plurality of fibres.

This same device 8 for measuring the fineness index also has a second orifice 6 connected via a second pipe 7 to a device 5 for measuring a differential pressure on either side of the said specimen. This device 5 for measuring the differential pressure is formed, for example, by a pressure regulator whose value is set and is kept constant at 254 mm Hg.

In a conventional "micronaire" apparatus (that is to say one designed to indicate "micronaire" values for fibres whose mean diameter lies within the 3 to 9 μm range), the device 8 for measuring the fineness index is formed by a transparent cylindrical tube of circular cross section, within which a movable indicator (of the "ludion" type) can move, this tube being graduated in "micronaire" value.

The device 5 for measuring the pressure differential is connected via a third pipe 9 to a device 10 for producing a constant flow of gas, it being possible for the gas to be conventionally air or nitrogen. Whatever the gas flow source used, the installation must allow the flow rate to be accurately controlled and the stability of the gas flow in the lower part of the measurement cell to be monitored.

The fluid flow source must deliver the fluid at flow rates such that the resulting velocities are low enough for the measured values of the resistance to the fluid flow to be independent of velocity.

To take an example, the flow source must be able to achieve fluid flow velocities possibly down to $0.5 \times 10^{-3}$ m/s.

As a variant, the "micronaire" apparatus shown in FIG. 1 includes a calibrated nozzle 12 at the orifice 6 or a calibrated nozzle 11 at the orifice 3. This calibrated member and especially the diameter of the orifices of the nozzle are determined when calibrating the "micronaire" apparatus under standard temperature and pressure conditions (T=20° C.; P=101 325 Pa).

The principle of the fineness index (or micronaire value) measurement is based on a measurement of the permeability of a porous, homogeneous and isotropic medium, a gaseous fluid flowing under laminar flow conditions through this porous medium (in this case a specimen of fibres whose mean diameter it is desired to determine).

The principle of the measurement is governed by Darcy's law:

$$v = \frac{Q}{S} = \frac{K}{\mu} \times \frac{\Delta P}{e} \quad (1)$$

v: velocity of the fluid (in m/s)
Q: flow rate of the fluid (in m$^3$/s)
S: flow area of the specimen through which the fluid flows perpendicularly (in m$^2$)
ΔP: differential pressure across the specimen (in N/m$^2$)
e: thickness of the specimen (in m)
μ: dynamic viscosity of the fluid (in N/m.s)
K: permeability (in m$^2$).

Studies carried out by Kozeny and Carman have shown that the coefficient K can be expressed in the following manner:

$$K = \frac{1}{j} \times \frac{\varepsilon^3}{(1-\varepsilon)^2} \times \frac{1}{(S_v)^2} \quad (2)$$

where:
K: permeability
j: structure factor $$\varepsilon: \text{porosity of the medium} = 1 - \frac{m}{\rho \times S \times e}$$

Sv: specific surface area
M: mass of the specimen
ρ: density of the specimen.

By combining equations (1) and (2) and by keeping the following parameters (density, porosity, structure factor, quantity of specimen introduced) constant, the flow rate Q varies inversely proportionally to the square root of the specific surface area according to the following equation:

$$Q = \frac{1}{(S_v)^2}$$

The method of operating the "micronaire" apparatus according to the invention is as follows.

Using an apparatus for determining the fineness of fibres of the prior art (that is to say one designed to deliver "micronaire" values for fibres whose mean diameter is substantially within the 3 to 9 μm range), and after having calibrated this apparatus with respect to a reference apparatus using a specimen of reference fibres, so as to obtain the curve shown in FIG. 2, the measurement cell 2 is filled with at least 5 g of fibres whose fineness it is desired to determine (these fibres being virgin fibres, that is to say containing no binder).

It should be pointed out the quantity of fibre introduced into the measurement cell is key. It has been noted that, with a quantity of fibre of less than 5 g (for example 3 g), especially when these fibres are hyperfine fibres, the latter do not occupy the entire volume of the measurement cell and preferential flow regions are created within the cell which singularly affect the measurement. Thus, it has been observed that the results of the measurement are not reproducible (more than 50% variation in the result).

In practice, tests have been carried out experimentally on various quantities of fibre and it was determined that the optimum quantity for obtaining satisfactory reproducibility of the measurement consists in taking at least 5 g of fibres.

The measurement cell 2 is filled with 5 g of virgin fibres, the mass of fibres being measured using a precision apparatus (the mass of fibres in fact lying within the 5.00±0.01 g range), this mass of fibres having been taken using a scoop, just after the fiberizing tool, and before the binder is deposited.

The measurement cell 2 is a cylindrical chamber whose characteristic dimensions are the following: Inside diameter: 25.4 mm; height: 25.4 mm, the opening of the cell being closed off by a cover 13.

The next step consists in regulating the static differential pressure between the upstream end and the downstream end of the specimen of fibres; by design, this pressure difference is set to 254 mm Hg.

The apparatus for determining the fineness according to the invention is connected to the device for producing the gas flow and the measurement is taken using the indicator of the volume flowmeter 20.

Plotted in FIG. 2, for various fibre manufacturing runs, corresponding to a range of three families of well-defined products, each of these families being characterized by the value of its thermal conductivity coefficient ($\lambda$), is the change in the thermal conductivity for various micronaire values, obtained by the apparatus forming the subject of the invention.

Thus, the following are defined:
fibres for light wound products (or IBR) having a density $M_v$, between 10 and 11 kg/m$^3$;
fibres for dense rolled products or for lightweight panels or partitions, having a density between 15 and 16 kg/m$^3$;
and finally, fibres for dense panels having a density between 22 and 23 kg/m$^3$.

By way of indication, it may be noted that there is a correspondence relationship between the micronaire values thus obtained and the mean diameter of the fibres of the specimen. In general, a micronaire value of about 12 l/min corresponds to a mean diameter of 2.5 to 3 μm, a value of 13.5 l/min correspond to approximately a mean diameter of 3 to 3.5 μm and finally 18 l/min corresponds to about 4 to 5 μm. It will be recalled that, for these three product ranges, the micronaire value (obtained by a conventional apparatus) cannot be obtained for a mean diameter of 2.5 to 3 μm, it is equal to approximately 2.7 for a mean diameter of 3 to 3.5 μm, and finally is equal to 3 for about 4 to 5 μm.

Of course, depending on the range of fibres whose mean diameter it is desired to characterize, it is possible to adapt the device for measuring the fineness (range of the volume flowmeter) so as to obtain the same measurement unit (l/min) for all desired fibre production runs.

Thus, for even finer fibres (mean diameter of the order of about 1 μm, or even less), it is possible with the apparatus forming the subject of the invention to obtain a reproducible and reliable value, namely of the order of 1 l/min.

The invention claimed is:

1. An apparatus for determining fineness index of mineral fibers, to deliver a micronaire value of fibers, the apparatus comprising:
a measurement cell configured to hold a specimen of a plurality of fibers;
a device for producing a fluid flow;
a device for measuring a differential pressure, on either side of the specimen, the device for measuring the differential pressure configured to be connected to the device for producing a fluid flow;
a device configured to measure the fineness index, the device comprising:
at least a first orifice connected to the measurement cell;
at least a second orifice connected to the device for measuring a differential pressure; and
at least one flowmeter configured to measure a volume flow rate of fluid passing through the measurement cell.

2. An apparatus according to claim 1, wherein the flowmeter is graduated in l/mm.

3. An apparatus according to claim 1, wherein the second orifice includes a calibrated member.

4. An apparatus according to claim 1, wherein the device configured to measure the fineness index is configured according to a range of fibers whose mean diameter it is desired to characterize.

5. A method of measuring fineness of mineral fibers, the method comprising:
filling a measurement cell with a specimen of fibers such that the specimen occupies an entire volume of the measurement cell so that there is no preferential flow of gas within the specimen;
adjusting a value of differential pressure between an upstream end and a downstream end of the specimen after the measurement cell has been closed using a lid;
connecting the measurement cell to a device for producing a flow of fluid; and
taking a measurement of fluid flow using at least one flowmeter.

6. A method according to claim 5, wherein the entire volume of the measurement cell is filled with a specimen of fibers, a mass of the specimen of fibers is equal to 5 g.

7. A method according to claim 5, wherein the mass of the specimen of fibers is between 5 and 10 g.

8. A method according to claim 5, wherein the value of the differential pressure is approximately 254 mmHg.

9. A method according to claim 5, wherein the mean fiber diameter of the specimen of fibers is less than 3 μm.

10. A method according to claim 5, wherein the specimen of fibers are insulation fibers of glass wool.

11. A method of measuring fineness of mineral fibers, the method comprising:
providing a measurement cell configured to hold a specimen of a plurality of fibers;
providing a device for producing a fluid flow;
providing a device for measuring a differential pressure, on either side of the specimen, the device for measuring the differential pressure connected to the device for producing a fluid flow;
providing a device configured to measure the fineness index, the device comprising at least a first orifice connected to the measurement cell; at least a second orifice connected to the device for measuring a differential pressure; and at least one flowmeter configured to measure a volume flow rate of fluid passing through the measurement cell;
filling the measurement cell with a specimen of fibers such that the specimen occupies an entire volume of the measurement cell so that there is no preferential flow of gas within the specimen;
adjusting a value of differential pressure between an upstream end and a downstream end of the specimen after the measurement cell has been closed using a lid;

connecting the measurement cell to the device for producing a flow of fluid; and taking a measurement of fluid flow using the at least one flowmeter.

12. A method according to claim 11, wherein the entire volume of the measurement cell is filled with a specimen of fibers, a mass of the specimen of fibers is equal to 5 g.

13. A method according to claim 11, wherein the mass of the specimen of fibers is between 5 and 10 g.

14. A method according to claim 11, wherein the value of the differential pressure is approximately 254 mmHg.

15. A method according to claim 11, wherein the mean fiber diameter of the specimen of fibers is less than 3 μm.

16. A method according to claim 11, wherein the specimen of fibers are insulation fibers of glass wool.

* * * * *